(12) United States Patent
Akiba et al.

(10) Patent No.: US 7,078,437 B2
(45) Date of Patent: Jul. 18, 2006

(54) APOLIPOPROTEIN D DEGRADATION INHIBITOR

(75) Inventors: Shunichi Akiba, Tochigi (JP); Katsutoshi Ara, Tochigi (JP); Hiroshi Kusuoku, Tochigi (JP); Yoshinori Nishizawa, Tochigi (JP)

(73) Assignee: Kao Corporation, Tokyo (JP)

( * ) Notice: Subject to any disclaimer, the term of this patent is extended or adjusted under 35 U.S.C. 154(b) by 127 days.

(21) Appl. No.: 10/899,155

(22) Filed: Jul. 27, 2004

(65) Prior Publication Data

US 2005/0049308 A1    Mar. 3, 2005

(30) Foreign Application Priority Data

Jul. 31, 2003    (JP) .............................. 2003-204836

(51) Int. Cl.
*A61K 31/20*    (2006.01)
(52) U.S. Cl. ..................................... 514/560
(58) Field of Classification Search ............... None
See application file for complete search history.

(56) References Cited

U.S. PATENT DOCUMENTS

| | | | | |
|---|---|---|---|---|
| 3,395,236 A | * | 7/1968 | White .......................... | 514/21 |
| 4,178,376 A | * | 12/1979 | Higuchi et al. ............. | 514/311 |
| 4,983,396 A | * | 1/1991 | Bodor et al. ................ | 424/449 |
| 5,034,414 A | * | 7/1991 | Wakabayashi et al. ...... | 514/549 |
| 5,284,657 A | * | 2/1994 | Lu et al. ...................... | 424/435 |
| 5,393,551 A | * | 2/1995 | Arcadipane .................. | 426/585 |
| 5,658,957 A | * | 8/1997 | Martin ........................ | 514/724 |
| 2003/0024011 A1 | * | 1/2003 | Dehesh et al. .............. | 800/281 |
| 2005/0196443 A1 | * | 9/2005 | Weinbach et al. .......... | 424/469 |

OTHER PUBLICATIONS

H. Kido, et al., "Inhibition of Chymase Activity by Long Chain Fatty Acids[1]", Archives of Biochemistry and Biophysics, vol. 230, No. 2, May 1, 1984, pp. 610-614.

C. Zeng, et al., "A human axillary odorant is carried by apolipoprotein D", Proc. Natl. Acad. Sci. USA, vol. 98, Jun. 1996, pp. 6626-6630.

E. A. Thomas, et al., "Increased CNS levels of apolipoprotein D in schizophrenic and bipolar subjects: Implications for the pathophysiology of psychiatric disorders", Proc. Natl. Acad. Sci. USA, vol. 98, No. 7, Mar. 27, 2001, pp. 4066-4071.

E. Rassart, et al., "Apolipoprotein D", Biochimica et Biophysics Acta, vol. 1482, 2000, pp. 185-198.

* cited by examiner

*Primary Examiner*—Raymond J. Henley, III
(74) *Attorney, Agent, or Firm*—Oblon, Spivak, McClelland, Maier & Neustadt, P.C.

(57) ABSTRACT

The invention contemplates drugs useful for maintenance or promotion at sites of regenerating nerves and for prevention or treatment of pathological conditions caused by denaturation or cell damage in the nervous system. Thus, the invention provides an apolipoprotein D degradation inhibitor containing lauric acid or oleic acid as an active ingredient.

1 Claim, 1 Drawing Sheet

APOLIPOPROTEIN D DEGRADATION INHIBITOR

FIELD OF THE INVENTION

The present invention relates to an apolipoprotein D degradation inhibitor, which inhibits or suppresses degradation of apolipoprotein D.

BACKGROUND OF THE INVENTION

Apolipoprotein D is a 29-kDa glycoprotein which is primarily associated with the high density lipoproteins (HDL) in human plasma. Apolipoprotein D is classified as belonging to the lipocalin family, on the basis of its primary structure. The apolipoprotein D gene is expressed in various tissues, with high levels expression in the adrenal gland, pancreas, kidneys, placenta, spleen, lungs, ovaries, testes, brain, peripheral nerves, and cerebrospinal fluid. Apolipoprotein D is also found in apocrine axillary secretions. Furthermore, apolipoprotein D was identified as the major component of the mammary cyst fluid from women with breast gross cystic disease.

Apolipoprotein D is degraded by proteases present in the living body or proteases produced by *Brevibacterium epiderumidis*, a resident skin flora.

Apolipoprotein D can bind various molecules such as cholesterol, steroid hormone, bilirubin, and arachidonic acid, depending on the conditions or the tissue (e.g., nerves) or organ. While neither its role nor its physiological ligand has been clearly identified, it is suggested that apolipoprotein D participates in maintenance and repair within the nervous system as a transporter of such molecules. (see for example, Eric Rassart et al., Biochimica et Biophysica Acta. 1482: 185–198, 2000).

It has been known that decrease can be found in total membrane phospholipids content, arachidonic acid (an essential fatty acid) content, cholesteryl esters in membranes from erythrocytes, red blood cells, and fibroblasts of schizophrenic patients. In addition, it has also been found that apolipoprotein D levels were significantly decreased in serum samples from schizophrenic patients as compared with normal subjects. (see for example, Thomas E A et al., Proc. Natl. Sci. USA, 98: 4066–4071, 2001).

Therefore, by suppressing degradation of apolipoprotein D to prevent decreasing of apolipoprotein D levels, schizophrenia or other diseases caused by denaturation or cell damage in the nervous system, such as Alzheimer's disease, Niemann-Pick disease type C (NPC), and Unverrichit-Lundborg disease can be effectively prevented or treated.

SUMMARY OF THE INVENTION

The present invention provides an apolipoprotein D degradation inhibitor containing lauric acid or oleic acid as an active ingredient.

The present invention also provides a method for inhibiting degradation of apolipoprotein D, comprising administering lauric acid or oleic acid to a subject.

DETAILED DESCRIPTION OF THE INVENTION

Figure 1:
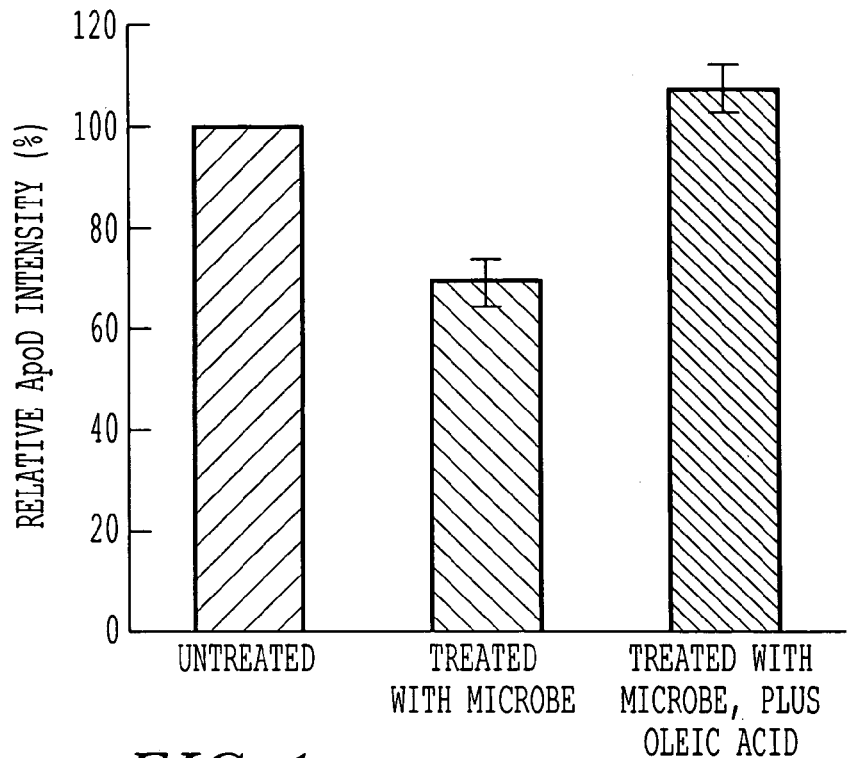
FIG. 1 shows inhibitory effect of oleic acid against degradation of apolipoprotein D.

The present invention is directed to a drug, which inhibits degradation of apolipoprotein D in living organisms, and thus is useful for maintenance or promotion at sites of regenerating nerves and for prevention or treatment of diseases caused by denaturation or cell damage in the nervous system. In view of the foregoing, the present inventors have searched among various natural products to locate components, which inhibit degradation of apolipoprotein D, and have found that certain fatty acids have an effect of inhibiting degradation of apolipoprotein D.

The apolipoprotein D degradation inhibitor of the present invention inhibits degradation of apolipoprotein D in living organisms, and therefore is useful as a drug for maintenance or promotion at sites of regenerating nerves or for prevention or treatment of schizophrenia or other diseases caused by denaturation or cell damage in the nervous system.

Both lauric acid and oleic acid—active ingredients of the apolipoprotein D degradation inhibitor of the present invention—are fatty acids which are found in almost all species of living organisms. Lauric acid and oleic acid also find utility in food products, and thus they are considered highly safe, even when administered for a long time.

Lauric acid and oleic acid may be produced from coconut oil, olive oil, cacao butter, palm oil, palm kernel oil, beef tallow, lard, sardine oil, herring oil, or similar substances. Alternatively, commercial products such as LUNAC L-55, LUNAC L-98, LUNAC O-A, LUNAC O-V, LUNAC O-LL-V, and LUNAC SO-90L may be employed.

Lauric acid and oleic acid may be employed singly or as a mixture of the two.

Apolipoprotein D can bind various molecules such as cholesterol, steroid hormone, bilirubin, and arachidonic acid, depending on the conditions or the tissue (e.g., nerves) or organ. While neither its role nor its physiological ligand has been clearly identified, it is suggested that apolipoprotein D participates in maintenance and repair within the nervous system as a transporter of such molecules. (see for example, Eric Rassart et al., Biochimica et Biophysica Acta. 1482: 185–198, 2000).

For example, the degeneration of nerves entails a release of cholesterol from the degradation of myelin sheaths, and a probable role of binding and transporting cholesterol and its esters in the peripheral nervous system is given to the apolipoprotein D for the maintenance of homeostasis and cholesterol utilization during regeneration. (see the above Eric Rassart et al., Biochimica et Biophysica Acta. 1482: 185–198, 2000). Apolipoprotein D is also considered to play a major role in redistribution of lipids after peripheral nerve injury. Furthermore, as it is known that bilirubin is produced in damaged nerves, one could speculate that the apolipoprotein D may prevent a local accumulation of this toxic molecule. (see the above Eric Rassart et al., Biochimica et Biophysica Acta. 1482: 185–198, 2000).

Apolipoprotein D plays similar functions in the central nervous system. For example, the levels of apolipoprotein D in the hippocampus and the cerebrospinal fluid of patients with Alzheimer's disease has been reported to be 60% higher and 350% higher, respectively, than those of healthy subjects of the same age. Although apolipoprotein D and apolipoprotein E levels have no correlation with each other, apolipoprotein D level in the cerebrospinal fluid of patients with Alzheimer's disease is affected by the apolipoprotein E genotype. Inheritance of an apolipoprotein E4 allele is correlated, in dose-dependent manner, with increased apolipoprotein D level in central nervous system if patients are with Alzheimer's disease. The apolipoprotein D increase in the presence of an E4 allele could be interpreted as a compensatory mechanism in peripheral nerve regeneration and central nervous system maintenance and repair. Specifically, increased apolipoprotein D expression in Alzheimer's disease could be linked to the ability of apolipoprotein D to function as a transporter of sterols, steroids, arachidonic acid in the brain that is implicated in tissue repair following injury(see the above Eric Rassart et al., Biochimica et Biophysica Acta. 1482: 185–198, 2000).

It has also been found that apolipoprotein D levels are significantly decreased in serum samples from schizophrenic patients as compared with healthy subjects.

The plasma level of apolipoprotein D in patients suffering from schizophrenia has been found to be lower than that of healthy subjects. This is in agreement with decresing of phospholipids content, cholesterol content, and arachidonic acid content (an essential fatty acid) in erythrocytes, fibroblasts, or similar cells of patients with schizophrenia, since apolipoprotein D can binds to arachidonic acid (the above Thomas E A et al., Proc. Natl. Sci. USA, 98: 4066–4071, 2001).

As described in Examples below, lauric acid or oleic acid inhibits or suppresses degradation of apolipoprotein D by proteases. Accordingly, degradation of apolipoprotein D can be prevented by administering to a subject an effective amount of lauric acid or oleic acid. Therefore, an apolipoprotein D degradation inhibitor containing an effective amount of lauric acid or oleic acid is useful as a drug for maintenance or promotion in peripheral nerve regeneration or for prevention or treatment of schizophrenia or other diseases caused by denaturation or cell damage in nervous system, such as Alzheimer's disease, Niemann-Pick disease type C (NPC), and Unverrichit-Lundborg disease.

Apolipoprotein D also serves as a carrier protein for an odor molecule, 3-methyl-2-hexenoic acid (3M2H). 3M2H has been reported to generate odor through the following mechanism. 3M2H binds with apolipoprotein D and is then secreted to the surface of the skin, where apolipoprotein D is degraded by proteases of resident skin flora present on the skin surface (Zeng C et al., Proc Natl Acad Sci USA, 93: 6626–6630, 1996). Therefore, the apolipoprotein D degradation inhibitor of the present invention is useful as a deodorant which prevents generation of body malodor.

The apolipoprotein D degradation inhibitor of the present invention may be formed into formulations for internal use (including tablets and capsules) or formulations for external use (including injections, ointments, liquids and solutions, extracts, lotions, emulsions, creams, gels, foams, essences, foundations, packs, sticks, powders, powder sprays, pump sprays, and sheets).

When the apolipoprotein D degradation inhibitor of the present invention is formed into a product for external use, any additives generally used for preparing drugs or cosmetic compositions may be incorporated. Examples of the additives include oils, surfactants, UV-ray absorbing agents, alcohols, chelating agents, pH-regulating agents, preservatives, thickeners, dyes, perfumes, skin nutrients, and a mixture thereof.

The apolipoprotein D degradation inhibitor of the present invention contains lauric acid or oleic acid in an amount of 0.001 to 50 wt. %, preferably 0.01 to 10 wt. %, more preferably 0.05 to 5 wt. %, still more preferably 0.1 to 0.5 wt. %, based on the entirety of the composition.

The dose of the apolipoprotein D degradation inhibitor of the present invention differs depending on dosage form and age, sex, body weight, of the patient, severity of the patient's condition, or other factors, and may be selected as appropriate. The daily dose of the inhibitor is preferably 1 to 1000 mg, more preferably 2 to 200 mg. The inhibitor is suitably administered once a day, or two to several times a day in a divided manner.

EXAMPLES

Example 1

Inhibitory Effect Against Degradation of Apolipoprotein D

Inhibitory effects of lauric acid and oleic acid on degradation of apolipoprotein D were studied using a human sweat concentrate as an apolipoprotein-D-containing sample and *Brevibacterium epiderumidis* cells as a protease.

(1) Preparation of Sweat Samples

The armpits of men exhibiting apocrine odor were wiped with absorbent cotton balls, each of which had been moistened with 1.5 mL of distilled water. The absorbent cotton balls were squeezed, whereby a solution (57.5 mL) was collected. The collected solution was filtered through a 0.45-µm filter and then concentrated by use of a MILLIPOR Centriprep YM-10.

Distilled water was added again to the concentrate, and the resultant solution was concentrated in a similar manner by use of a Centriprep YM-10, to thereby remove substances of low molecular weight. The product was employed as a sweat concentrate.

Figure 2:
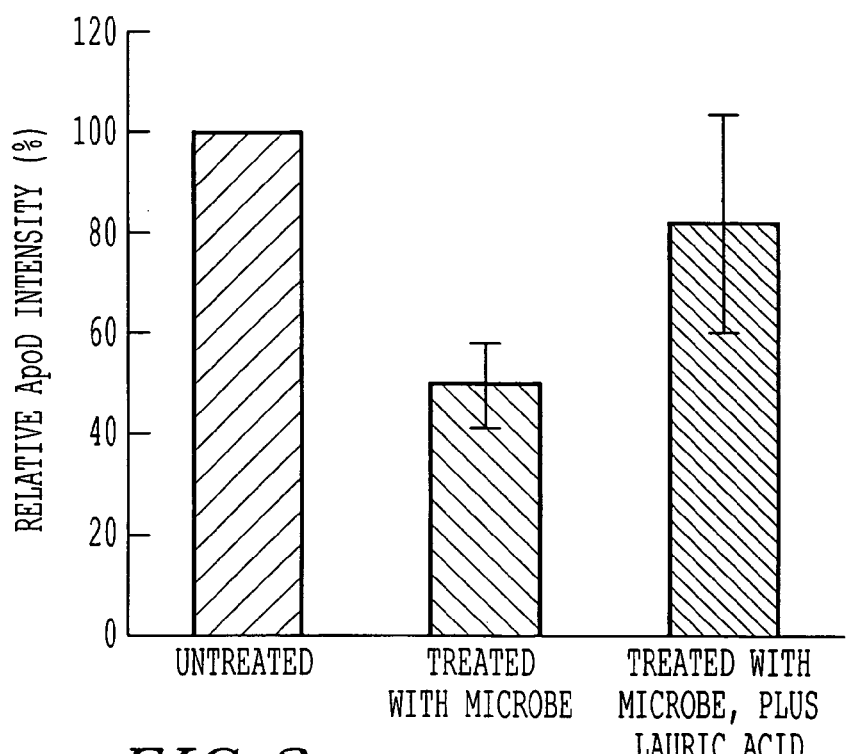
FIG. 2 shows inhibitory effect of lauric acid against degradation of apolipoprotein D.

(2) 100 mM Tris-HCl buffer (0.03 mL), distilled water (0.02 mL), and each of lauric acid (Sigma) and oleic acid (Sigma) were added to an aliquot (0.04 mL) of the sweat concentrate prepared through the above method (1). To the mixture, *Brevibacterium epiderumidis* cells which had been washed 3 times with 20 mM Tris-HCl buffer (pH 7.2) were inoculated such that a final cell count of about $10^8$ cfu/mL was achieved, followed by incubation at 37° C. for 24 hours. Thereafter, antibody-staining was performed through the following procedure. Briefly, the cell-treated sweat concentrate was subjected to SDS polyacrylamide electrophoresis (SDS-PAGE) by use of a Ready Gel J (15% of separation gel concentration, Bio-Rad Laboratories, Inc.), and the thus-separated proteins were electrically transcribed from the gel onto a PVDF filter (Millipore Corporation, Immobilon transfer membrane). Apolipoprotein D was antibody-stained through use of an anti-apolipoprotein D monoclonal mouse antibody (RDI) as a primary antibody and an HRP-labeled anti-mouse Ig antibody (Amersham Pharmacia Biotech) as a secondary antibody. Apolipoprotein D was detected by use of an ECL Plus western blotting detection system (Amersham Pharmacia Biotech), and percent residue of apolipoprotein D; i.e., (amount of apolipoprotein D in sample)÷(amount of apolipoprotein D in untreated sweat)×100, was calculated through image processing. The results are shown in FIGS. 1 and 2.

When the sweat concentrate was treated with *Brevibacterium epiderumidis* cells, apolipoprotein D in the sweat concentrate was degraded, and the amount thereof decreased. In contrast, when lauric acid or oleic acid was added to the concentrate, degradation of apolipoprotein D was suppressed.

The invention claimed is:

1. A method for inhibiting degradation of apolipoprotein D in a mammal in need thereof, comprising administering to said mammal, a pharmaceutical composition comprising from 0.1 to 0.5% by weight on the basis of said composition, of lauric acid or oleic acid, whereby said degradation is inhibited.

* * * * *